(12) United States Patent
Joo

(10) Patent No.: US 9,901,608 B2
(45) Date of Patent: Feb. 27, 2018

(54) COMPOSITION AND METHOD FOR ENHANCING ALCOHOL METABOLISM

(71) Applicant: GANGNEUNG-WONJU NATIONAL UNIVERSITY INDUSTRY ACADEMY COOPERATION GROUP, Gangwon (KR)

(72) Inventor: Seong-Soo Joo, Gyeonggi-do (KR)

(73) Assignee: GANGNEUNG-WONJU NATIONAL UNIVERSITY INDUSTRY ACADEMY COOPERATION GROUP, Gangneung-si, Gangwon (KR)

(*) Notice: Subject to any disclaimer, the term of this patent is extended or adjusted under 35 U.S.C. 154(b) by 139 days.

(21) Appl. No.: 14/471,996

(22) Filed: Aug. 28, 2014

(65) Prior Publication Data

US 2015/0283192 A1    Oct. 8, 2015

(30) Foreign Application Priority Data

Apr. 7, 2014   (KR) .................. 10-2014-0041409

(51) Int. Cl.
A61K 36/258        (2006.01)

(52) U.S. Cl.
CPC ........ A61K 36/258 (2013.01); *A61K 2236/00* (2013.01)

(58) Field of Classification Search
CPC ................... A61K 2236/00; A61K 36/258
See application file for complete search history.

(56) References Cited

U.S. PATENT DOCUMENTS

| | | | |
|---|---|---|---|
| 9,314,493 B2* | 4/2016 | Park ............. | A61K 36/258 |
| 2002/0136785 A1* | 9/2002 | Yuan ............. | A61K 31/704 |
| | | | 424/728 |
| 2008/0286388 A1* | 11/2008 | Shiao ............. | A23G 3/36 |
| | | | 424/728 |
| 2010/0256198 A1* | 10/2010 | Megiddo ......... | A61K 31/44 |
| | | | 514/343 |
| 2012/0328545 A1* | 12/2012 | Park ............. | A61Q 19/08 |
| | | | 424/62 |

FOREIGN PATENT DOCUMENTS

| | | | |
|---|---|---|---|
| JP | 2011-219370 A | | 11/2011 |
| KR | 2009116623 A | * | 11/2009 |
| KR | 1020100021369 A | | 2/2010 |
| KR | 20120005195 A | * | 7/2010 |
| KR | 1020110078525 A | | 7/2011 |
| KR | 10112513 B1 | | 3/2012 |
| KR | 1020120138392 A | | 12/2012 |

OTHER PUBLICATIONS

Park et al. Increase in Insulin Secretion Induced Bypanax Ginseng Berry Extracts . . . Journal of Ginseng Research vol. 36, No. 2, 153-160 (2012).*
Lee et al. Chemical Constituents and Biological Activities of the Berry of Panax Ginseng; J. Med. Plants Res. vol. 4(5), pp. 349-353 (2010).*
Anoja S. Attele, et al; "Antidiabetic Effects of Panax ginseng Berry Extract and the Identification of an Effective Component", Diabetes, vol. 51, Jun. 2002, pp. 1851-1858.
Arthur I. Cederbaum, et al; "CYP2E1 Sensitizes the Liver to LPS-and TNF α-Induced Toxicity via Elevated Oxidative and Nitrosative Stress and Activation of ASK-1 and JNK Mitogen-Activated Kinases", International Journal of Hepatology, vol. 2012, Article ID 282790, 19 pages, Epub Oct. 18, 2011.
David W. Crabb, et al; "Overview of the role alcohol dehydrogenase and aldehyde dehydrogenase and their variants in the genesis of alcohol-related pathology", Proceedings of the Nutrition Society, The Summer Meeting of the Nutrition Society was held at King's College, London on Jul. 7-10, 2003, pp. 49-63, vol. 63, Feb. 2004.
RA Deitrich, et al; "Removal of acetaldehyde from the body", Novartis Found Symp. 2007; vol. 285; pp. 23-40; discussion 40-51, 198-9 (Abstract Only Provided).
B.-Y. Kim, et al; "Effects of Asparagus officinalis Extracts on Liver Cell Toxicity and Ethanol Metabolism", Journal of Food Science, vol. 74, No. 7, Sep. 2009, pp. H204-H208.
Kosfost; "Innovations in Food Service for Human Well-Being", Annual Meeting Korean Society of Food Service and Technology, Aug. 28-30, 2013; 2 pages.
You-Gui Li, et al; "Pharmacology and Cell Metabolism Saponins from Panax japonicus Protect Against Alcohol-Induced Hepatic Injury in Mice by Up-regulating the Expression of GPX3, SOD1 and SOD3", Alcohol & Alcoholism, vol. 45, No. 4, pp. 320-331, Advance Access Publication Jun. 16, 2010.
Ca Marco, et al; "Acute intoxication", Emerg. Med. Clin. North Am. Nov. 1990; vol. 8(4); pp. 731-748 (Abstract Only Provided).
Neil R. McGregor; "Pueraria lobata (Kudzu root) hangover remedies and acetaldehyde-associated neoplasm risk", Alcohol, vol. 41, pp. 469-478; Nov. 2007.
R. Swift, et al; "Alcohol hangover: mechanisms and mediators", Alcohol Health Res World; vol. 21(1), pp. 54-60; Jan. 1998.
Luisa Vonghia, et al; "Acute alcohol intoxication", European Journal of Internal Medicine, vol. 19, pp. 561-567; Available online Apr. 2, 2008.
Jeffrey G. Wiese, MD, et al; "The Alcohol Hangover", Ann. Intern. Med. vol. 132, No. 11; pp. 897-902; Jun. 6, 2000.

* cited by examiner

*Primary Examiner* — Chris R Tate
*Assistant Examiner* — Aaron J Kosar
(74) *Attorney, Agent, or Firm* — Ladas & Parry LLP; Loren K. Thompson

(57) ABSTRACT

Disclosed is a composition for enhancing alcohol metabolism in a subject, who overdrank, the composition comprises an effective amount of ginsenoside-free extract of steam-dried Korean ginseng berry (GFM) and one or more pharmaceutically or sitologically acceptable carriers. The composition of the present disclosure may be effective for alleviating hangover according to overdrink and for protecting liver from alcoholic injure.

5 Claims, 11 Drawing Sheets

COMPOSITION AND METHOD FOR ENHANCING ALCOHOL METABOLISM

GOVERNMENT INTEREST

The present disclosure was supported by a grant of the Korean Healthcare Technology R&D Project, the Ministry of Health and Welfare, Republic of Korea (Grant No. A091121).

CROSS-REFERENCE TO RELATED PATENT APPLICATION

This application claims the benefit of priority to Korean Patent Application No. 10-2014-0041409 filed with the Korean Intellectual Property Office on Apr. 7, 2014, the disclosure of which is incorporated herein in its entirety by reference.

FIELD OF THE DISCLOSURE

The present disclosure relates to a composition and a method for enhancing alcohol metabolism, and particularly, to a composition for enhancing alcohol metabolism of a subject who overdrank and a method for enhancing alcohol metabolism using the same.

BACKGROUND OF THE DISCLOSURE

Korean ginseng (*Panax ginseng* C. A. Meyer) which is a partial shade-tolerant plant belonging to family Araliaceae has been used as medicinal herb because of its various pharmaceutical effects. There are various ginsenosides which are saponins in Korean ginseng. The saponins are classified with panaxadiol (PD), panaxatriol (PT) and oleanane. In addition, there are non-ginsenoside compounds including carbohydrates such as starch, antioxidant aromatic compound such as polyacethylene, gomisin N-A, and acidic peptides having insulin-like activity.

The root of ginseng is a commonly used herbal medicine and alternative therapeutic materials; however, very little work has been done to evaluate the effect of the unripened ginseng berry. Several studies have reported that the ginseng berry contains higher concentrations of biologically active ginsenosides than that of other ginseng parts (Attele A. S. et al., *Diabetes* 51:1851-1858, 2002).

Alcohol (ethanol, $CH_3CH_2OH$) consumption is used as a psychoactive drug and is one of the oldest recreational drugs used by humans. However, the use of a large volume of ethanol can lead to intoxication and has effects on the liver, heart, pancreas, and nervous system (Vonghia L. et al., *Eur. J. Intern. Med.* 19:561-567, 2008). Ethanol is rapidly absorbed mainly in the proximal intestinal tract (70% in the stomach and 25% in the duodenum) as it easily crosses cell membranes (Marco C. A. et al., *Emerg. Clin. North Am.* 8:731-748, 1990). The high levels of alcohol dehydrogenase (ADH) during ethanol metabolism, which is the primary defense against alcohol, detoxify ethanol in the liver and stomach (Crabb D. W. et al., *Proc. Nutr. Soc.* 63:49-63, 2004). The enzymes, ADH, cytochrome P450 (CYP2E1), and catalase convert ethanol into acetaldehyde which is further metabolized by mitochondrial aldehyde dehydrogenase (ALDH) to acetate (Swift R. and Davidson D., *Alcohol Health Res. World* 22:54-60, 1998). Among these enzymes, the CYP2E1 pathway results in a significant increase in reactive oxygen species (ROS), including superoxide, hydrogen peroxide and hydroxyl radical which can lead to further hepatocyte damage via oxidative stress (Cederbaum A. I. et al., *Int. J. Hepatol.* 2012:582790, 2012). Many reports have suggested that acetaldehyde, a chemically reactive toxic substance, is responsible for alcohol hangover, which can cause vasodilation, flushing of the face, nausea, and headache although alcohol-induced electrolyte imbalance, hypoglycemia, dehydration also induce a serial hangover (Swift R. and Davidson D., *Alcohol Health Res. World* 22:54-60, 1998; Wiese J. G. et al., *Ann. Intern. Med.* 132: 897-902, 2000; Deitrich R. A. et al., *Novartis Found Symp.* 285: 23-40, 2007). As hangover symptoms usually continue for up to 8-24 h, many treatments are focused on shortening its duration along with reducing symptom severity. In addition, lowering the blood acetaldehyde concentration would potentially be a therapeutic target for hangover by increasing ADH levels (McGregor N. R., *Alcohol* 41:469-78, 2007). Several studies on alleviating hangover symptoms via antioxidant and ADH/ALDH stimulant effects have been conducted using various natural sources such as ginseng root, green tea, asparagus, and a combination of natural extracts (Kim B. Y., et al., *J. Food Sci.* 74: H204-208, 2009; Li Y. G. et al., *AlcoholAlcohol* 45:320-331, 2010; Korean Patent No. 1125130; and Japanese Patent Gazette No. 2011-219370).

SUMMARY OF THE DISCLOSURE

However, the compositions described in the prior arts have problems such as relative low effect and high cost for manufacturing. The present disclosure is devised to solve various problems including the problems described above. Thus the object of the present disclosure is to provide a more effective and economical composition and a method for enhancing alcohol metabolism in a subject who overdrank.

In an aspect to the present disclosure, a composition for enhancing alcohol metabolism in a subject who overdrank, the composition comprises an effective amount of ginsenoside-free extract of steam-dried Korean ginseng berry (GFM) and one or more pharmaceutically or sitologically acceptable carriers is provided.

In another aspect to the present disclosure, a pharmaceutical composition for treating liver disease in a subject, the composition comprises a therapeutically effective amount of ginsenoside-free extract of steam-dried Korean ginseng berry and one or more pharmaceutically acceptable carriers is provided.

In still another aspect to the present disclosure, a method for enhancing alcohol metabolism in a subject who overdrank, the method comprises administering an effective amount of ginsenoside-free extract of steam-dried Korean ginseng berry to the subject.

DETAILED DESCRIPTION OF THE DISCLOSURE

Figure 1:
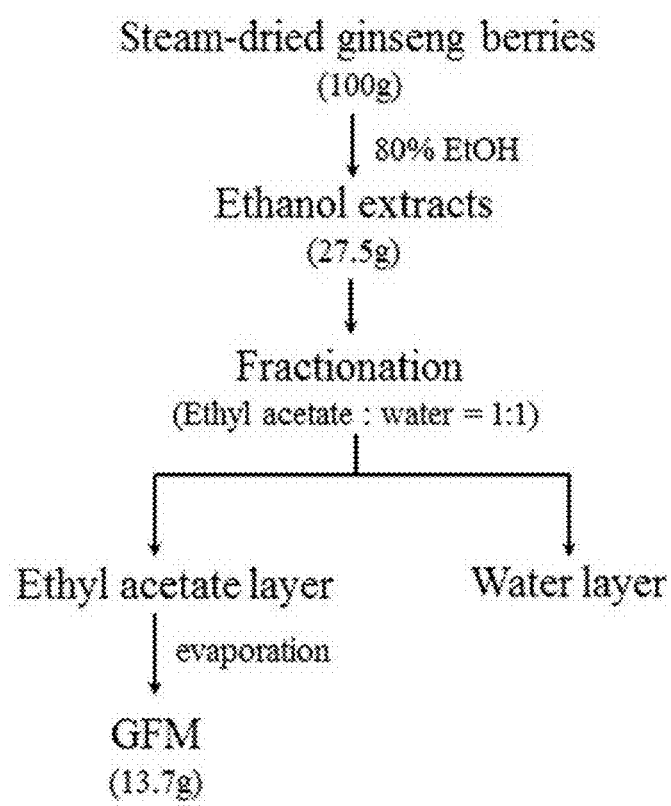
FIG. 1 is a schematic diagram illustrating an exemplary procedure for preparing the ginsenoside-free extract of steam-dried Korean ginseng berry of the present disclosure.

In an aspect to the present disclosure, a composition for enhancing alcohol metabolism in a subject who overdrank, the composition comprises an effective amount of ginsenoside-free extract of steam-dried Korean ginseng berry (GFM) and one or more pharmaceutically or sitologically acceptable carriers is provided.

According to the composition, the ginsenoside-free extract of steam-dried Korean ginseng berry (GFM) may be prepared by the following method:

steaming Korean ginseng berry;
drying the steam-dried Korean ginseng berry;
grinding the dried steam-dried Korean ginseng berry;
preparing steam-dried Korean ginseng berry extract by extracting the powder of steam-dried Korean ginseng berry using water, lower grade alcohol of C1 to C4 or aqueous solution thereof;
fractionating the steam-dried Korean ginseng berry extract as ethylacetate layer and water layer after adding ethylacetate and water to the steam-dried Korean ginseng berry extract; and
separating and drying the ethylacetate layer.

The Korean ginseng berry may be immature berry and may be harvested from 4 to 6 year-old Korean ginseng.

The lower grade alcohol may be methanol, ethanol or n-propanol or iso-propanol.

The composition may be a pharmaceutical composition or a nutraceutical composition.

The pharmaceutical composition of the present disclosure may be administrated orally or parenterally. When administrated parenterally, the composition may be administrated by intravenous injection, intranasal injection, intramuscular injection, intraperitoneal injection, or subcutaneous injection, etc.

In addition, the pharmaceutical composition may be administrated with a dosage of 0.1 mg/kg to 1 g/kg. The dosage may be adjusted according to patient's age, sex and condition.

The pharmaceutical composition may be formulated with various formulations, such as liquid formulation contained in a retort pouch, or a power formulation, a tablet formulation, and a capsule formulation after hot air drying or freeze drying or a gel formulation using a gelation agent like gelatin. Any other pharmaceutical formulation may be used as needed.

In addition, one or more pharmaceutically acceptable carriers may be used for the formulation of the pharmaceutical composition of the present disclosure. These carries may be conventional organic or inorganic carries such as an excipient, a lubricant, a binder and a disintegrating agent when the composition is a solid formulation, or a solvent, a solubilizing agent, an emulsifying agent, an isotonifying agent, a buffering agent, and a soothing agent may be used when the composition is a liquid formulation. Moreover, one or more additives such as a conventional preservative, an antioxidant, a coloring agent, a sweetening agent, an absorbent, and a wetting agent may be used as needed.

The nutraceutical composition may be formulated as various formulations suitable for nutraceutical products such as a liquid formulation, a powder formulation, a pellet formulation, a capsule formulation, a tablet formulation (a coated tablet, a sugarcoated tablet, a sublingual tablet, etc.), and jelly formulation.

In another aspect to the present disclosure, a pharmaceutical composition for treating liver disease in a subject, the composition comprises a therapeutically effective amount of ginsenoside-free extract of steam-dried Korean ginseng berry and one or more pharmaceutically acceptable carriers is provided.

According to the pharmaceutical composition, the Korean ginseng berry may be immature berry and may be harvested from 4 to 6 year-old Korean ginseng.

According to the pharmaceutical composition, the liver disease may be autoimmune hepatitis, primary biliary cirrhosis, liver fibrosis, non-alcoholic fatty liver disease, fatty liver disease, alcoholic fatty liver disease, alcoholic hepatitis, acute fatty liver disease, lover cirrhosis, or liver cancer.

In still another aspect to the present disclosure, a method for enhancing alcohol metabolism in a subject who overdrank, the method comprises administering an effective amount of ginsenoside-free extract of steam-dried Korean ginseng berry to the subject.

According to the method, the Korean ginseng berry may be immature berry and may be harvested from 4 to 6 year-old Korean ginseng.

According to the method, the ginsenoside-free extract of steam-dried Korean ginseng berry may be administrated orally or parenterally.

The terms used in this document are defined as follows:

The term used in the document, the "ginsenoside-free extract of steam-dried Korean ginseng berry" or "ginsenoside-free molecule (GFM)" means an extract of steam-dried Korean ginseng berry whose ginsenosides are substantially removed. The term "substantially removed" means particular components are contained in an amount under the detection limit or in an amount not showing any biological effect.

The term, "ginsenoside" means a class of steroidglycosides, and triterpene saponins, found exclusively in the plant genus *Panax* (ginseng). The ginsenosides are classified with two groups, the Rb1 group (characterized by the protopanaxadiol presence: Rb1, Rb2, Rc and Rd) and the Rg1 group (protopanaxatriol: Rg1, Re, Rf, and Rg2).

Hereinafter, the present disclosure is described in detail with reference to following examples and experimental examples. However, the present disclosure is not limited to following examples and experimental examples and the present disclosure may be embodied in many different embodiments. Thus, the following examples and experimental examples are provided in order to fully disclose the present disclosure and fully inform the scope of the disclosure to a person skilled in the art.

Example 1: Extraction of Korean Ginseng Berry

Fresh Korean ginseng (*Panax ginseng* C. A. Meyer) berries were obtained from Korea Genetic Pharm Co. Ltd. (Gyeonggi, Republic of Korea). All unripened berries were gathered from at least 4-year-old plants, and whole ginseng berries were steam-dried at 100° C. for 2 h and dried for 24 h at 50° C. These steaming and drying procedures were repeated four to seven times and were then combined, and the final products were prepared after 7 days of drying. Finely ground steam-dried ginseng berries (100 g) were steeped in 1 L of 80% aqueous ethanol for 24 h repeatedly for 3 days at room temperature. The ethanol extracts were combined, filtered through filter paper (Whatman International Ltd., Maidstone, UK), and evaporated. The ethanol extracts were fractionated using a mixture of ethyl acetate and water (1:1 ratio), and then the ethyl acetate layer was evaporated to obtain ethyl acetate fraction (FIG. 1). FIG. 1 is a schematic diagram of an exemplary procedure for preparing steam-dried Korean ginseng berry extract. 50% of ethyl acetate fraction (13.7 g) was obtained from 27.5 g of ethanol extract.

Example 2: Gas Chromatogtaphy-Mass Spectrometry (GC-MS)

Figure 2:
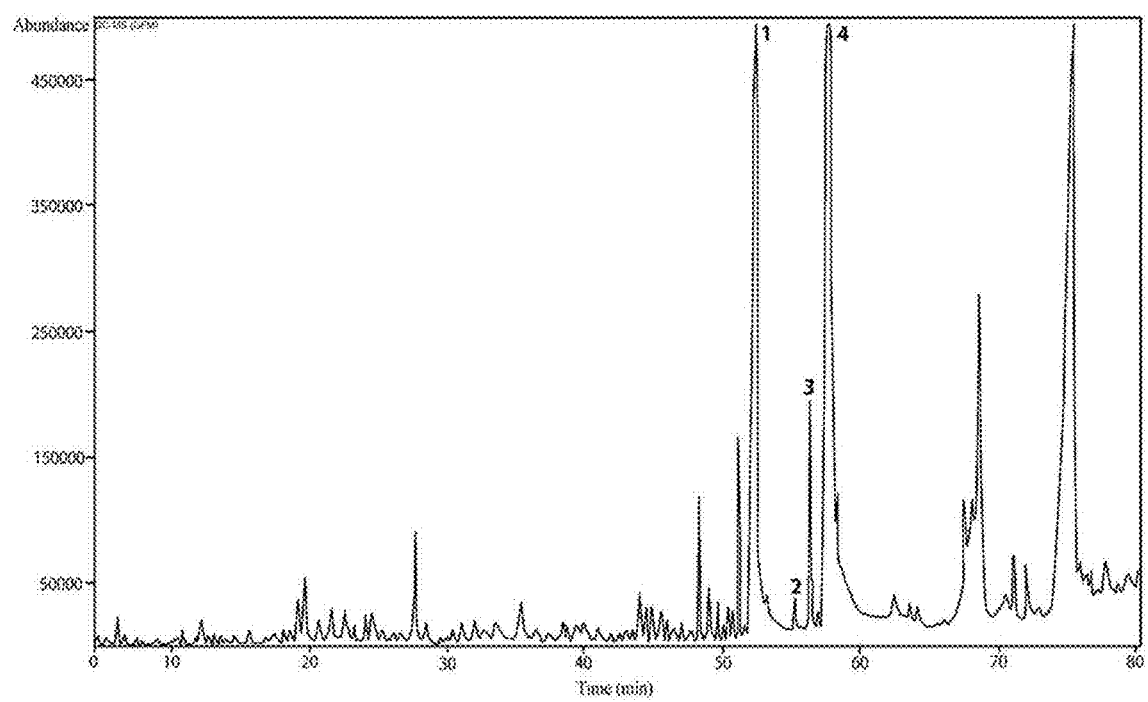
FIG. 2 is a chromatogram of GC-MS of the ginsenoside-free extract of steam-dried Korean ginseng berry of the present disclosure.

The ethyl acetate fraction was dissolved in ethanol and identified with an analytical Agilent Technologies 5975C GC/MS instrument (Agilent Technologies, USA) equipped with a CTC CombiPAL autosampler system. Chromatographic separation was carried out using helium carrier gas on an HP-5 column (250 μm×0.25 μm×30 m, Agilent Technologies, USA). A 10 μL aliquot of the sample was injected into a split injector that was operated in split mode using a 5:1 split ratio with split flow and column flow of 5 mL/min and 1 mL/min, respectively. The injector temperature was held at 250° C., and the transfer line was 250° C. The GC oven was held at 50° C. for 3 min, ramped at 2° C./min to 280° C. and held for 3 min (serum ethanol was detected at 50° C. for 3 min, ramped at 10° C./min to 150° C. and held for 3 min). The ion source temperature was 250° C. with electron impact ionization energy of −70 V. Data were collected from 35 m/z to 250 m/z using a detector voltage of 1,059 V following a 4 min delay. The components were identified by comparing their relative retention times and mass spectra with Wiley7N library data of the GC-MS system. FIG. 2 is a chromatogram of GC-MS of the ethyl acetate fraction of steam-dried Korean ginseng berry of the present disclosure. As shown in FIG. 2, the ethyl acetate fraction contained various components of over 50 s. The most abundant compounds in the ethyl acetate fraction were PA (30.00%), methyl linoleate (34.10%), and LA (34.66%), accounting for about 98.76% of the ethyl acetate fraction. Table 2 shows that biologically active molecules (butanoic acid, PA, HA, methyl linoleate, and LA). Interestingly, there is no detectable ginsenosides. Thus, the inventor designated the ethyl acetate fraction as "ginsenoside-free molecules (hereinafter referred as to "GFM")"

TABLE 1

GC-MS library of GFM[a]

| Peak | RT(min) | molecules | Qulity (%) | % Area |
|---|---|---|---|---|
| 1 | 52.482 | Palmitic acid (PA) | 99 | 30.00 |
| 2 | 55.286 | Heptadecanoic acid (HA) | 99 | 0.11 |
| 3 | 56.337 | Methyl linoleate (MLA) | 99 | 34.10 |
| 4 | 57.667 | Linoleic acid (LA) | 97 | 34.66 |

[a]Components were identified based on a comparison of their relative retention times and mass spectra using the Wiley 7N library data from the GC-MS system.

Experimental Example 1: Radical Scavenging Assay and Protein Protection Assay 1-1: Radical Scavenging Assay DPPH is usually used as a reagent to evaluate the free radical scavenging activity of various antioxidant substances. DPPH is a stable free radical and accepts an electron or hydrogen radical to become a stable diamagnetic molecule. Thus, to evaluate free radical scavenging activity, fractions were allowed to react with the DPPH solution (Espin J. C. et al., *J. Agric. Food Chem.*, 48:648-656, 2000). Each lyophilized fraction was dissolved in dimethyl sulfoxide (DMSO, Sigma-Aldrich) as a stock solution (100 mg/mL) and each fraction was reacted with 0.3 mM DPPH in methanol. Various concentrations of GFM (0.01-100 μg/mL) were reacted with the DPPH radical solution for 30 min at room temperature. Absorbance was then measured at 517 nm. DPPH free radical scavenging activity was calculated using the following equation:

$$\text{DPPH scavenging activity (\%)} = [Ac - (A - As)]/Ac \times 100,$$

wherein Ac is the absorbance of the control DPPH solution, A is absorbance of the sample with the DPPH solution, and As is absorbance of the sample.

Figure 3:
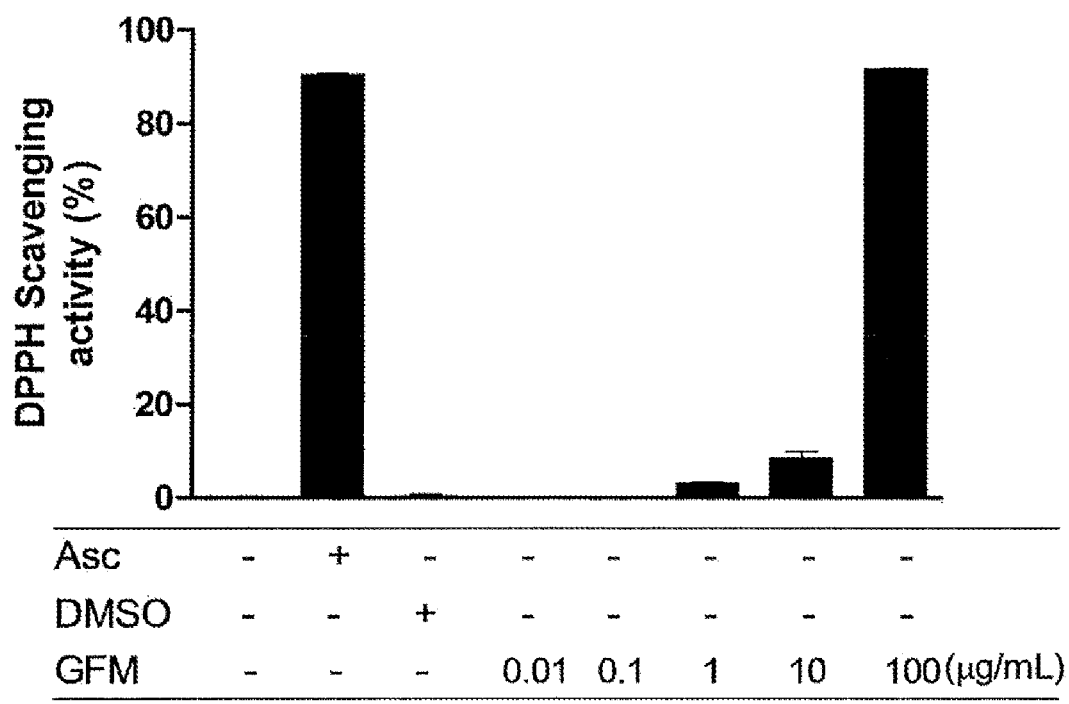
FIG. 3 is a graph showing free radical scavenging activity of the GFM according to an embodiment of the present disclosure.

In the DPPH assay, GFM began to show radical scavenging activity at 1 μg/mL and reached a maximum activity at 100 μg/mL as much as that of the positive control, ascorbic acid (FIG. 3).

1-2: Protein Protection Assay

For the protein protection assay, hydroxyl radical-mediated oxidation experiments were performed using a metal-catalyzed reaction, as described previously with some modifications (Mayo J. C. et al., *Biochim. Biophys. Acta.*, 1620: 139-150, 2003). Particularly, the target protein, bovine serum albumin (BSA), was dissolved in a 150 mM phosphate buffer (pH 7.3) to a final concentration of 0.5 mg/mL. The BSA solution was incubated with and without 100 μM copper ($Cu^{2+}$) and 2.5 mM $H_2O_2$ in the presence and absence of the samples. The control antioxidant was 50 μM ascorbate, which was directly dissolved in PBS. The reactions were carried out in open tubes and placed in a shaking water bath maintained at 37° C. After the reaction was complete, each mixture was separated on a 10% sodium dodecyl sulfate-polyacrylamide gel electrophoresis (SDS-PAGE), and stained with 0.1% Coomassie Blue solution (FIG. 4).

Figure 4:
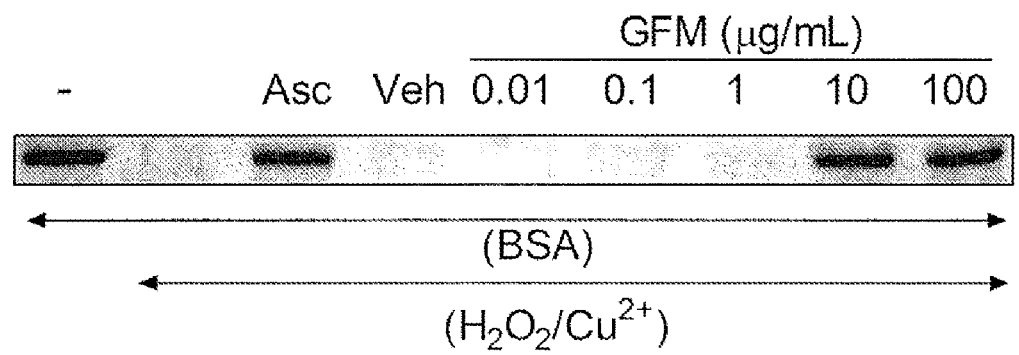
FIG. 4 is a PAGE (polyacrylamide gel electrophoresis) profile of BSA protein incubated with or without the GFM according to an embodiment of the present disclosure and $Cu^{2+}/H_2O_2$.

As shown in FIG. 4, the hydroxyl radical-mediated oxidation assay which determines protein-level antioxidant properties perfectly protected BSA protein degradation from the attack of hydroxyl radicals produced by $Cu^{2+}$ and $H_2O_2$ from 10 μg/mL GFM (FIG. 4). Thus, it was confirmed that the GFM may scavenge free radicals such as DPPH radicals and hydroxyl free radicals from the result of FIGS. 3 and 4. This suggests that GFM may have multifunctional ethanol detoxifying activity through antioxidant effect.

Experimental Example 2: Cytotoxicity and Cytoprotection 2-1: Cell Culture

HepG2 human hepatoma cells (Korean Cell Line Bank, Seoul, Republic of Korea) were grown in RPMI1640 complete medium (Hyclone, Logan, Utah, USA) supplemented with 10% fetal bovine serum, 100 U/mL penicillin, and 100 μg/mL streptomycin (Invitrogen, Carlsbad, Calif., USA). The cultures were maintained under 5% $CO_2$ at 37° C. in tissue culture flasks. For all experiments, cells were grown to >90% confluency and subjected to no more than 20 cell passages. The medium was changed every 2-3 days. Subconfluent cells were harvested and seeded at a density of $5 \times 10^5$ cells or $1.5 \times 10^6$ cells in poly-L-lysine-coated 35 mm or 60 mm culture plates. After plating for 24 h, the medium was replaced with serum-free Dulbecco's Modified Eagle's medium (DMEM), washed once with phosphate buffered saline (PBS), and treated with GFM, or the positive controls of palmitic acid (PA), heptadecanoic acid (HA), linoleic acid (LA) (Sigma-Aldrich, St. Louis, Mo., USA) and a commercially available anti-hangover drink containing the fruit extract of *Hovenia dulcis*, glutathione, and taurine with other natural herbal extracts (CDT). The CDT whose trademark is "Condition" is a product of CJ Cheiljedang company and was purchased from a pharmacy.

2-2: Cytotoxicity Assay

Cytotoxicity of the GFM was investigated by measuring lactate dehydrogenase (LDH) release from HepG2 cells. That is, the cytotoxicity induced by the GFM in HepG2 cells was quantified by measuring LDH release at varying ranges of concentration (1-1,000 μg/mL). Cytotoxicity in experimental samples was determined as % LDH release, and the data from triplicate cultures were expressed as the mean±standard deviation. Concentration-dependent cytotoxicity determined as % LDH release was compared with non-treated control cells (Ctrl) and $H_2O_2$ (1 mM)-treated control was used as a positive control. LDH content was determined using a commercial non-radioactive LDH assay kit, CytoTox 96® (Promega, Madison, Wis., USA), which is based on a coupled enzymatic reaction that results in conversion of tetrazolium salt into a red formazan product. The increase in the amount of formazan produced in the culture supernatant directly correlates with the increase in the number of lysed cells. Formazan was quantified spectrophotometrically by measuring its absorbance at 490 nm (Spectra Max 340, Molecular Devices, Sunnyvale, Calif., USA).

Figure 5:
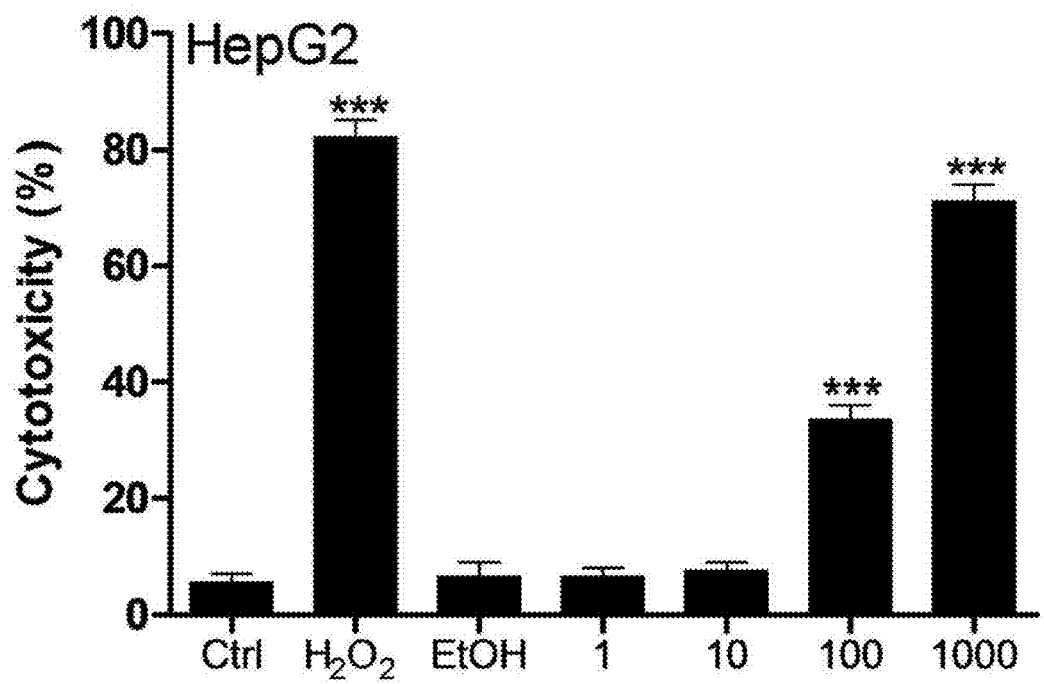
FIG. 5 is a graph showing cytotoxicity of $H_2O_2$ and ethanol to HepG2 cells.

As shown in FIG. 5, incubating HepG2 cells with GFM did not result in cytotoxicity at about 10 μg/mL, and ethanol (200 mM) was also not cytotoxic (FIG. 5).

2-3: Cytoprotection

Figure 6:
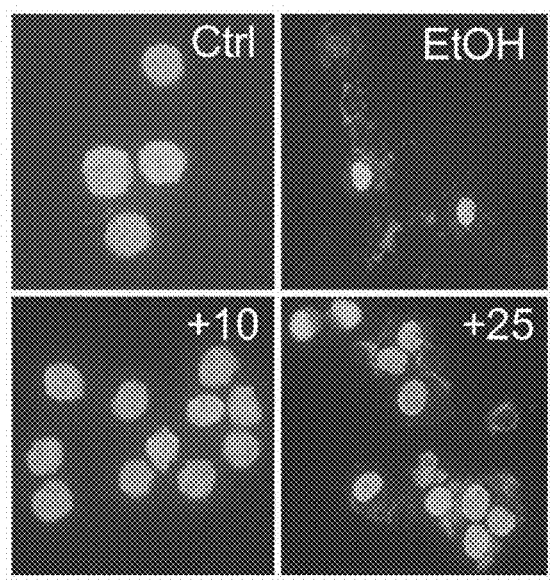
FIG. 6 is a series of fluorescent microscopic images of nuclear morphology of HepG2 cells treated with or without ethanol and stained with DAPI.

The cells were stained with 4',6-diamidino-2-phenylindole dihydrochloride hydrate (DAPI) (Sigma-Aldrich) to observe the effect of cytoprotection by GFM 30 min after co-incubation of GFM and 0.5 mM ethanol. The slides were stained with DAPI (1:500 dilution in PBS) for 10 minutes in the dark at room temperature, fixed in 4% paraformaldehyde in PBS, and visualized with an inverted fluorescent microscope system (Eclipse Ti-S; Nikon, Tokyo, Japan) at a magnification of ×600. As shown in FIG. 6, the GFM (10 and 25 μg/mL) successfully protected cells from a high concentration of ethanol (0.5 M) compared to a single treatment of ethanol.

Experimental Example 3: Effect of GFM on Major Metabolic Genes and Identification of Effective Molecules 3-1: Quantitative Realtime Polymerase Chain Reaction (qPCR) Analysis To evaluate the role of the GFM in ethanol metabolism, the genes of primary enzymes (ADH, ALDH, CYP2E1, and catalase) involved in eliminating ethanol from the body were quantified by real-time qPCR. Particularly, total RNA extracts from HepG2 cells ($1 \times 10^6$ cells/well) treated with ethanol (0.2 mM) or GFM (10 μg/ml) were prepared using the Trizol method (Invitrogen) after 1, 2, 4 and 24 h after the treatment. And then, cDNA was synthesized from RNA by reverse transcription of 1 μg of total RNA using the Improm-II reverse transcription system (Promega) and oligo dT primers in a total volume of 20 μL. PCR amplification was performed using the primers described in Table 1 (Bioneer, Deajeon, Republic of Korea). Quantitative real-time PCR reactions were run on a Rotor-Gene 6000 (Corbett Research, Sydney, Australia) using SYBR Green PCR Master Mix (Qiagen, Valencia, Calif., USA) in 20 μL reaction mixtures. Each real-time-PCR master mix contained 10 μL 2× enzyme mastermix, 7.0 μL RNase free water, 1 μL of each primer (10 μM each) and 1 μL diluted template. The PCR was performed with an initial pre-incubation step for 10 min at 95° C., followed by 45 cycles of 95° C. for 15 s, annealing at 52° C. for 15 s, and extension at 72° C. for 10 s. Melting curve analysis was used to confirm formation of the expected PCR product, and products from all assays were additionally tested with 1.2% agarose gel electrophoresis to confirm the correct lengths. An inter-run calibrator was used, and a standard curve was created for each gene to obtain PCR efficiencies. Relative sample expression levels were calculated using Rotor-Gene 6000 Series Software 1.7 and were expressed relative to glyceraldehyde 3-phosphate dehydrogenase and corrected for between-run variability. Data for the experimental samples were expressed as a percentage of the internal control gene. All experiments were performed in triplicate and the results were shown as mean±standard deviation. *P<0.05, P<0.01, * P<0.001. Ctrl means control and EtOH means ethanol-treating group.

Figure 7:
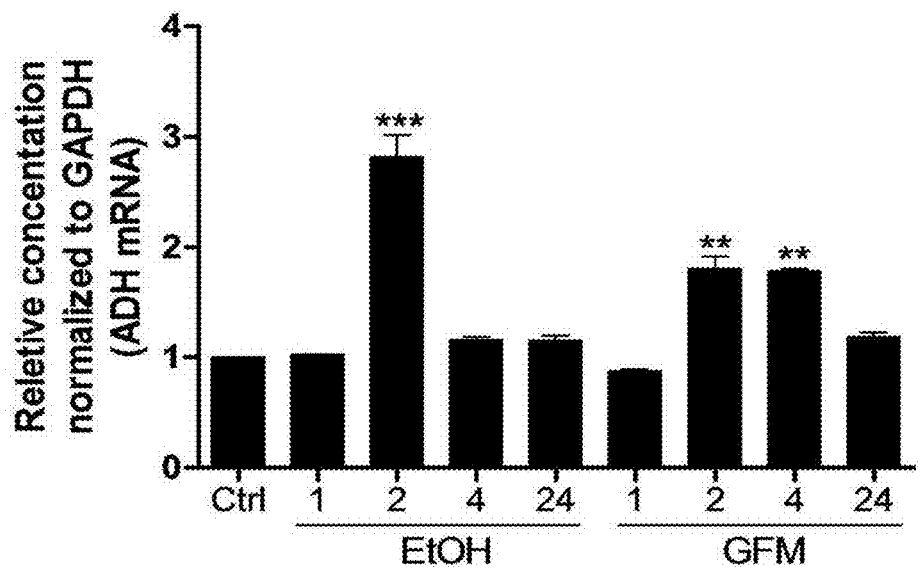
FIG. 7 is a graph showing effect of the GFM according to the present disclosure on ADH (alcohol dehydrogenase) gene among genes involved in alcohol metabolism.
Figure 8:
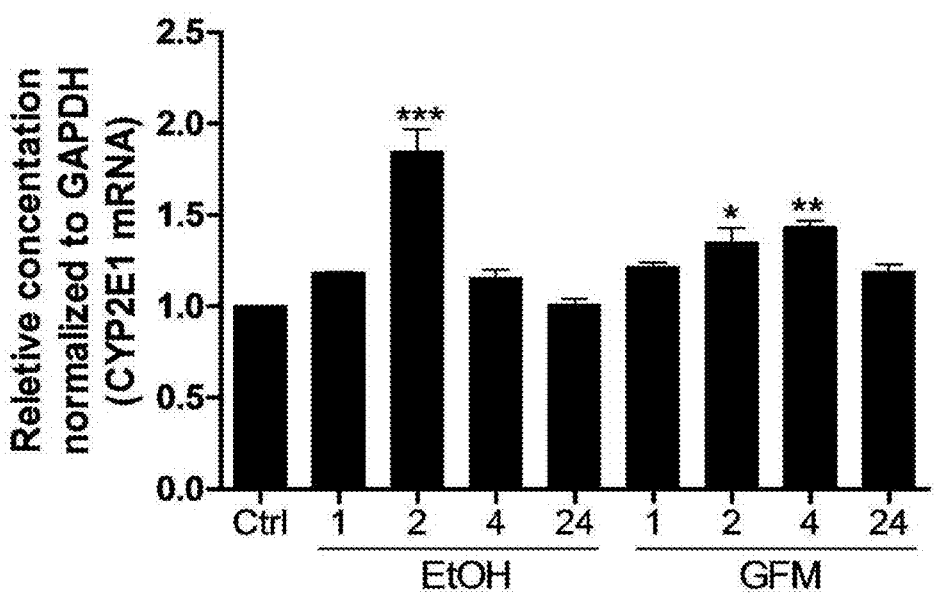
FIG. 8 is a graph showing effect of the GFM according to the present disclosure on CYP2E1 (cytochrome p450 2E1) gene among genes involved in alcohol metabolism.
Figure 9:
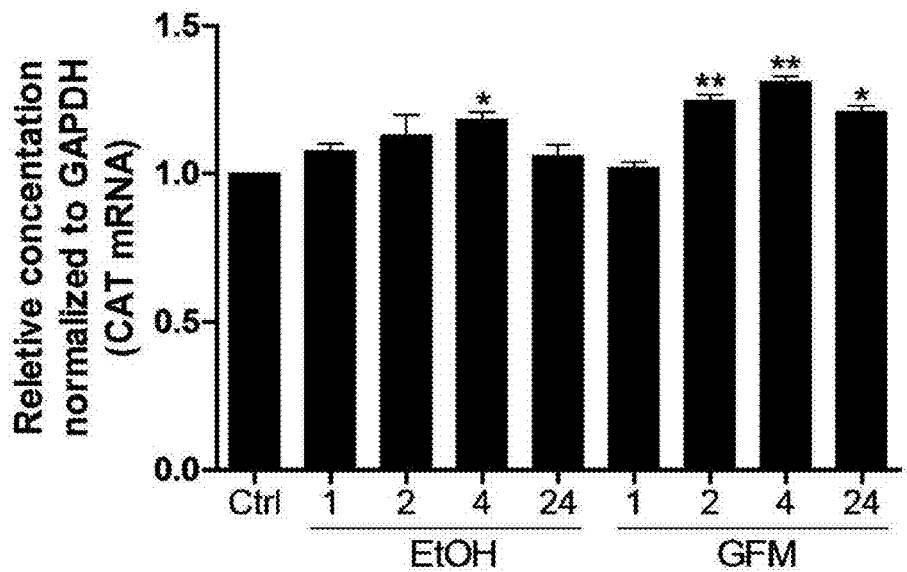
FIG. 9 is a graph showing effect of the GFM according to the present disclosure on CAT (catalase) gene among genes involved in alcohol metabolism.
Figure 10:
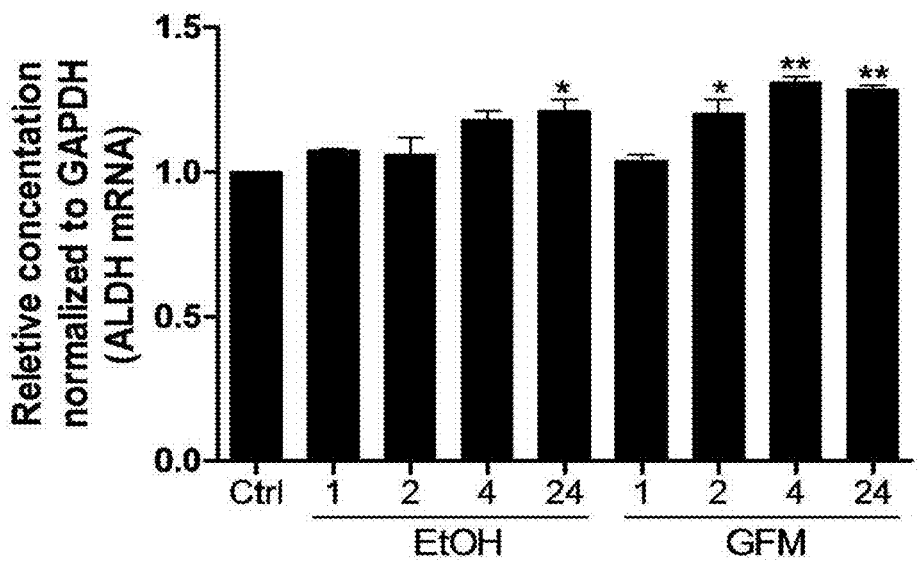
FIG. 10 is a graph showing effect of the GFM according to the present disclosure on ALDH (acetaldehyde dehydrogenase) gene among genes involved in alcohol metabolism.

As shown in FIGS. 7-9, ADH, CYP2E1, and catalase genes, which all contribute to oxidative metabolism of ethanol, were stimulated by GFM alone. Interestingly, GFM stimulated these genes 2 h after the treatment as did ethanol and the increase continued up to 4 h. Moreover, the GFM did significantly stimulate the ALDH gene, a major metabolizer of acetaldehyde in the mitochondria, to acetate and NADH (FIG. 10). These results suggest that the GFM according to an embodiment of the disclosure is effective to enhance alcohol metabolism.

These data suggest that GFM may be involved in oxidative pathways of ethanol metabolism, and, thus, play an effective role in ethanol detoxification including alcohol hangover.

relative humidity: 50%, light/dark cycle: 12 h) for 1 week. The animal experiments were approved by the Gangneung-Wonju National University Animal Care and Use Committee (approval no. GWNU-2013-9), and all procedures were conducted in accordance with the Guide for Care and Use of Laboratory Animals published by the National Institutes of Health. Stabilized mice were randomly allocated into four experimental groups: non-treated control, positive control (CDT), ethanol alone, and ethanol+GFM group (n=5). GFM (10 and 25 mg/kg) and CDT (0.5 mL/mouse) were administered 1 h before ethanol administration and blood samples were collected 1 h after ethanol administration. Perfused liver tissues from the treated mice were prepared using the Trizol method (Invitrogen, USA). And then, mRNA of cytochrome p450 (CYP2E1), catalase (CAT), and acetaldehyde dehydrogenase (ALDH), which are major enzymes involved in ethanol metabolism were quantified using real-time RT-PCR as described in Experimental example 3-1. As

TABLE 2

Primers used for qPCR analysis

| Name of primers | Species | Gene | Nucleotide sequences | length (bp) | GenBank Accession No. | SEQ ID NO |
|---|---|---|---|---|---|---|
| hADH1B F | Human | ADH1B | 5'-GTGGATGAGAATGCAGTGGC-3' | 278 | NM_000668 | 1 |
| hADH1B R | | | 5'-CATTCAGTGGCACCCAACTC-3' | | | 2 |
| hALDH1A1 F | | ALDH1A1 | 5'-GGAGCCAAAAGGGTCATCAT-3' | 203 | NM_000689 | 3 |
| hALDH1A1 R | | | 5'-GTGATGGCATGGACTGTGGT-3' | | | 4 |
| hCatalase F | | Catalase | 5'-CAGCTGACACAGTTCGGGAC-3' | 276 | NM_001752 | 5 |
| hCatalase R | | | 5'-GATGTCCATCTGGAATCCCC-3' | | | 6 |
| hCYP2E1 F | | CYP2E1 | 5'-CATGAAGCAACCCGAGACAC-3' | 277 | NM_000773 | 7 |
| hCYP2E1 R | | | 5'-CTGCAAAATGGCACACAACA-3' | | | 8 |
| hGAPDH F | | GAPDH | 5'-GGAGCCAAAAGGGTCATCAT-3' | 203 | AK_026525 | 9 |
| hGAPDH R | | | 5'-GTGATGGCATGGACTGTGGT-3' | | | 10 |
| mADH1B F | Mouse | ADH1B | 5'-ATTTCATGGGCGTCAGTTCA-3' | 209 | NM_011996 | 11 |
| mADH1B R | | | 5'-AAGACCTACACACCCCAGGC-3' | | | 12 |
| mALDH1A1 F | | ALDH1A1 | 5'-GTGGACAAAGTGGCGTTCAC-3' | 200 | NM_009656 | 13 |
| mALDH1A1 R | | | 5'-ACTGGCCCTGGTTGAAGAAC-3' | | | 14 |
| mCatalase F | | Catalase | 5'-CAGCGACCAGATGAAGCAGT-3' | 197 | NM_009804 | 15 |
| mCatalase R | | | 5'-CAGGAATCCGCTCTCTGTCA-3' | | | 16 |
| mCYP2E1 F | | CYP2E1 | 5'-CTGCATGGCTACAAGGCTGT-3' | 162 | NM_021282 | 17 |
| mCYP2E1 R | | | 5'-ACTTAGGGAAAACCTCCGCA-3' | | | 18 |
| mGAPDH F | | GAPDH | 5'-TACAGCTTCACCACCACAGC-3' | 187 | NM_007393 | 19 |
| mGAPDH R | | | S'-AAGGAAGGCTGGAAAAGAGC-S' | | | 20 |

3-2: Identification of Effective Molecules

Figure 11:
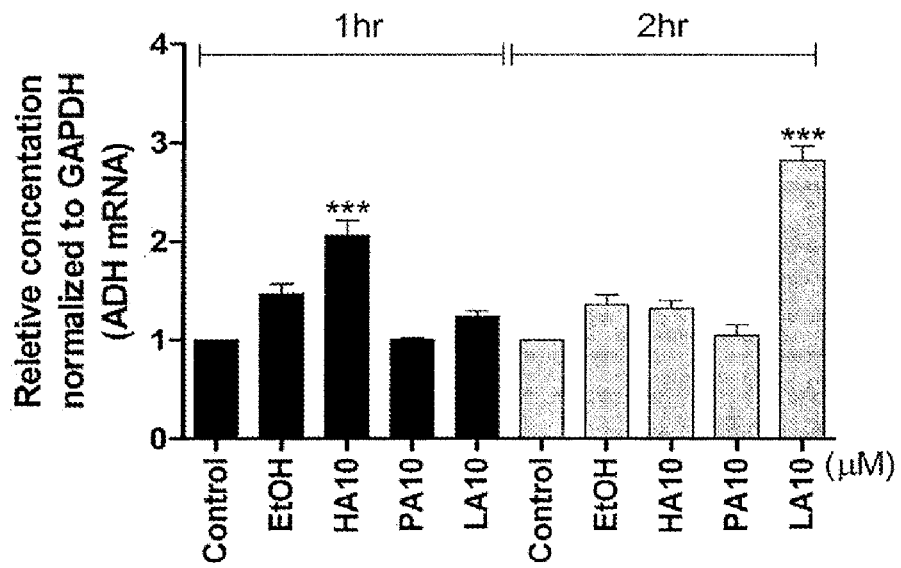
FIG. 11 is a graph showing mRNA expression of ADH induced by fatty acid (HA, PA and LA) quantitatively
Figure 12:
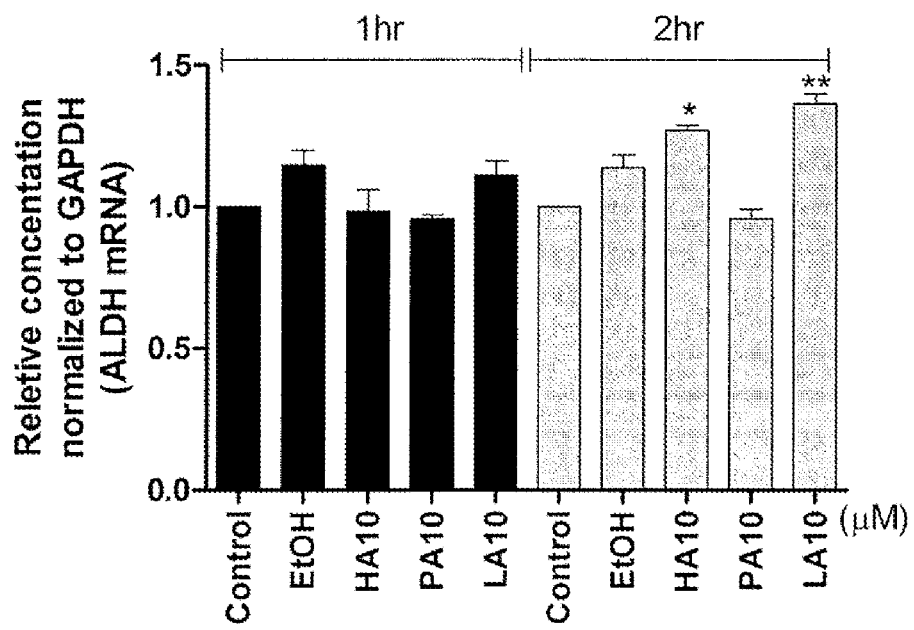
FIG. 12 is a graph showing mRNA expression of ALDH induced by fatty acid (HA, PA and LA) quantitatively

To understand what components of the GFM affected primary gene expression, three major molecules (HA, PA and LA) identified in the GFM were investigated under the same conditions of Experimental example 3-1. Particularly, total RNA extracts from HepG2 cells (1×10⁶ cells/well) treated with ethanol (0.2 mM) or three major molecules (HA, PA and LA) (10 μM) identified from GFM were prepared using the Trizol method (Invitrogen) after 1, and 2 h after the treatment. And then the mRNA of ADH and ALDH were quantified using real-time RT-PCR as described in Experimental example 3-1. The results demonstrated that the effectiveness of GFM might be mainly from LA, which is an unsaturated fatty acid (FIGS. 11 and 12).

Experimental Example 4: Analysis of Effect of GFM on Ethanol Metabolism In Vivo 4-1: Analysis of Major Metabolic Enzymes (CYP2E1, CAT and ADLH)

Figure 13:
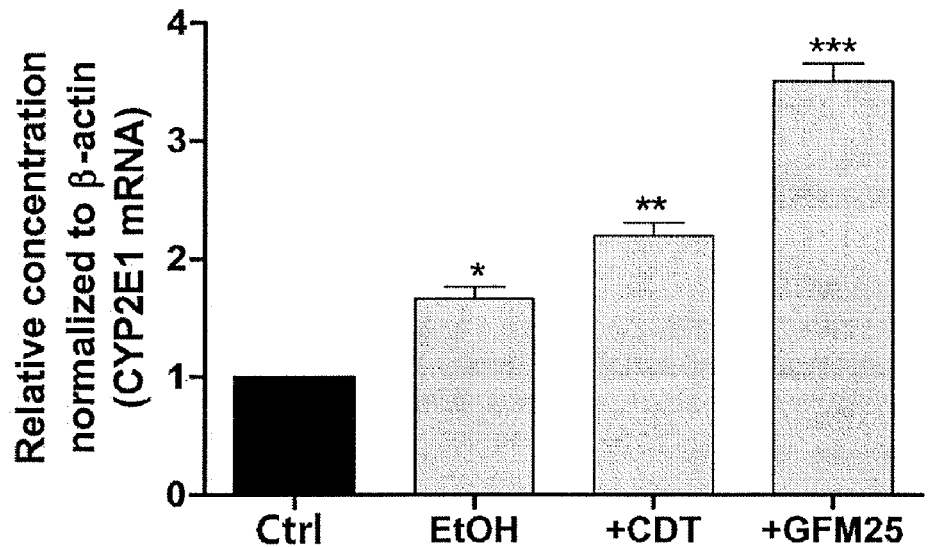
FIG. 13 is a graph showing mRNA expression of CYP2E1 in livers of mice (control (Ctrl), administered with ethanol only (EtOH), or with ethanol and a commercially available hangover reliever (+CDT) or the ginsenoside-free extract of steam-dried Korean ginseng berry according to the present disclosure (+GFM)).
Figure 14:
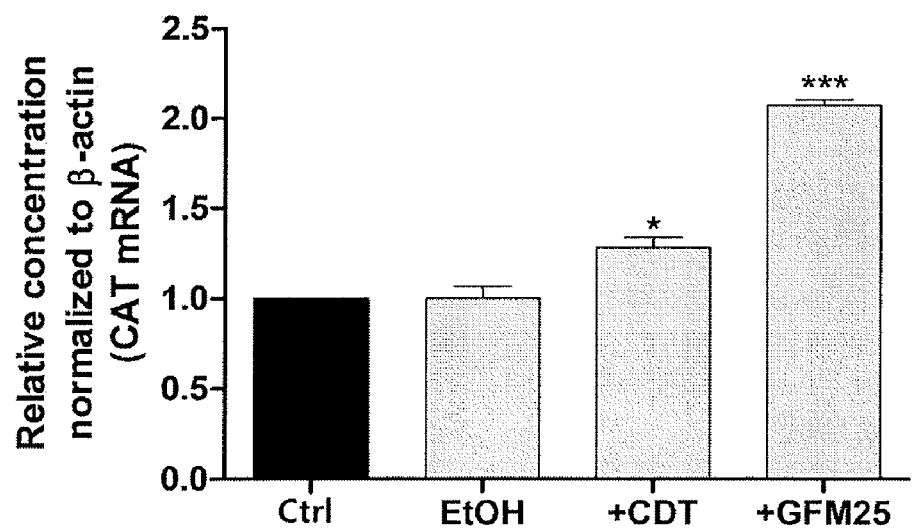
FIG. 14 is a graph showing mRNA expression of catalase in livers of mice (control (Ctrl), administered with ethanol only (EtOH), or with ethanol and a commercially available hangover reliever (+CDT) or the ginsenoside-free extract of steam-dried Korean ginseng berry according to the present disclosure (+GFM)).
Figure 15:
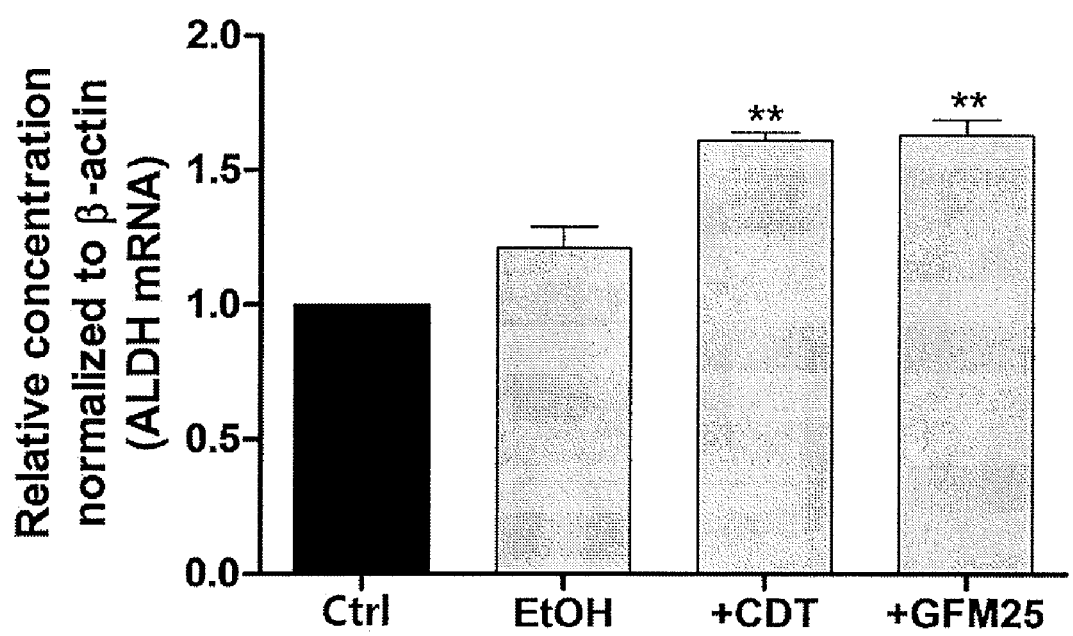
FIG. 15 is a graph showing mRNA expression of ALDH in livers of mice (control (Ctrl), administered with ethanol only (EtOH), or with ethanol and a commercially available hangover reliever (+CDT) or the ginsenoside-free extract of steam-dried Korean ginseng berry according to the present disclosure (+GFM)).

Male BALB/c mice (7-week old) were purchased from Samtaco (Osan, Kyunggi-do, Republic of Korea), and were adapted to laboratory conditions (temperature: 20±2° C., shown in FIGS. 13-15, the primary genes (CYP2E1, catalase, and ALDH) involved in ethanol metabolism were significantly elevated much higher in liver tissue when treated with CDT and the GFM than those of ethanol-treated mice. In particular, CYP2E1 and catalase mRNA, which contribute to primary oxidative metabolism of ethanol, were remarkably expressed (p<0.001), suggesting rapid ethanol removal (FIGS. 13 and 14). ALDH mRNA, which converts acetaldehyde to nontoxic acetate in mitochondria, was also increased by the GFM (FIG. 15)

4-2: Analysis of Serum Levels of Acetaldehyde and Ethanol

Figure 16:
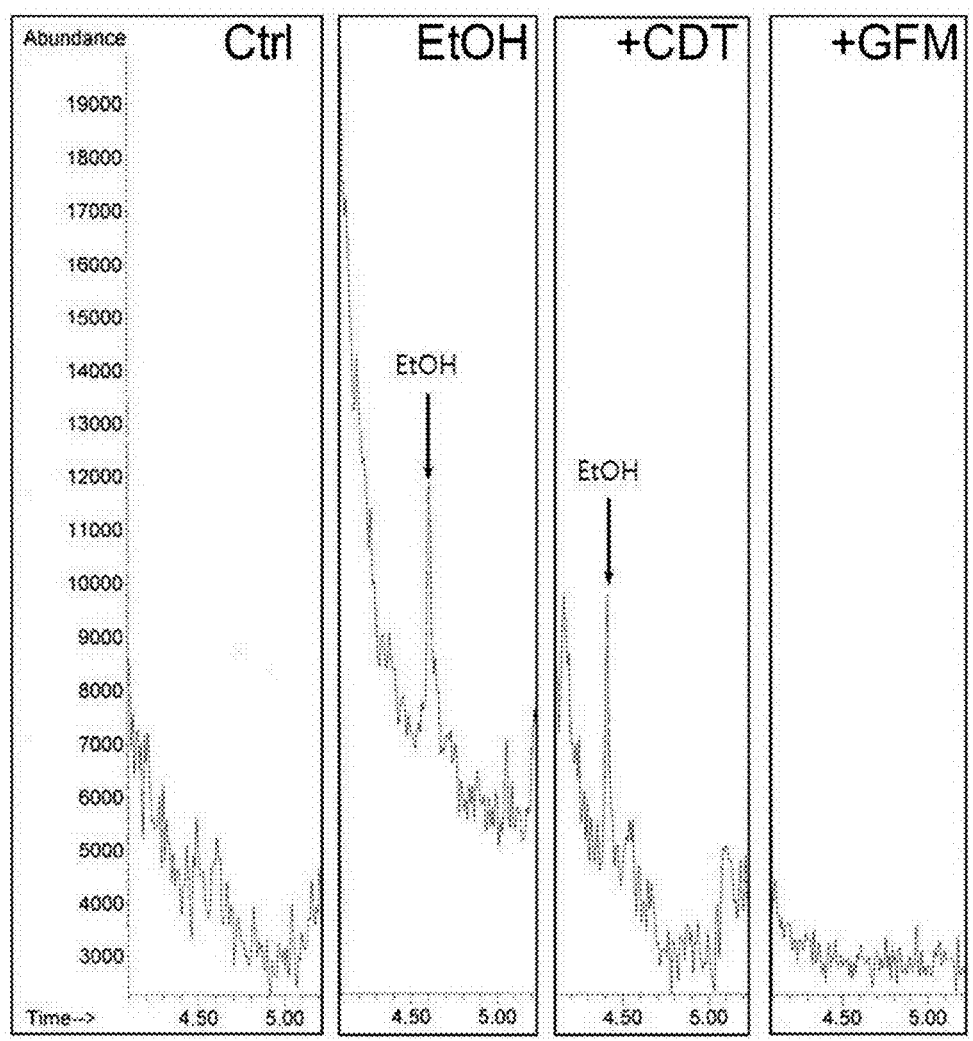
FIG. 16 is a chromatogram of GC-MS chromatography of serum of mice (control (Ctrl), administered with ethanol only (EtOH), or with ethanol and a commercially available hangover reliever (+CDT) or the ginsenoside-free extract of steam-dried Korean ginseng berry according to the present disclosure (+GFM)).
Figure 17:
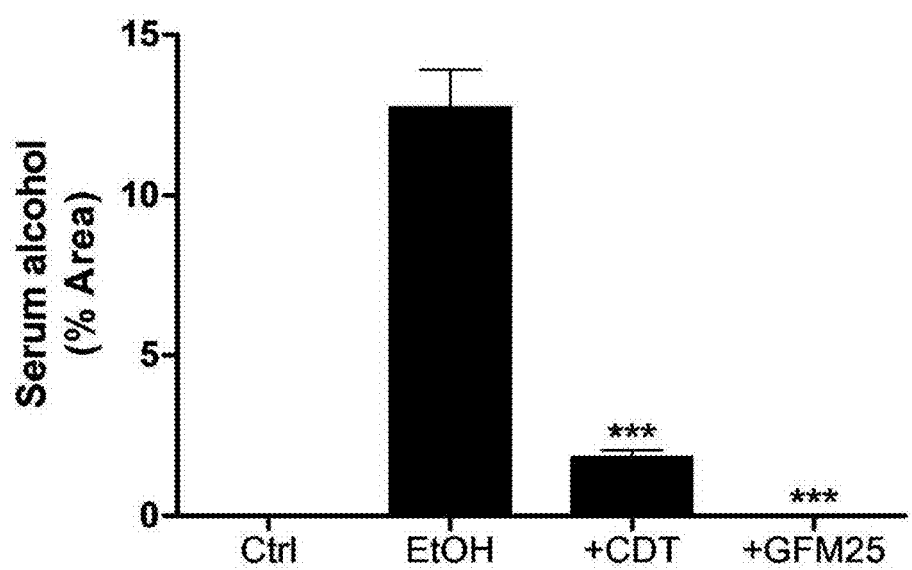
FIG. 17 is a graph showing serum ethanol level of BALB/c mice (control (Ctrl), administered with ethanol only (EtOH), or with ethanol and a commercially available hangover reliever (+CDT) or the ginsenoside-free extract of steam-dried Korean ginseng berry according to the present disclosure (+GFM)).
Figure 18:
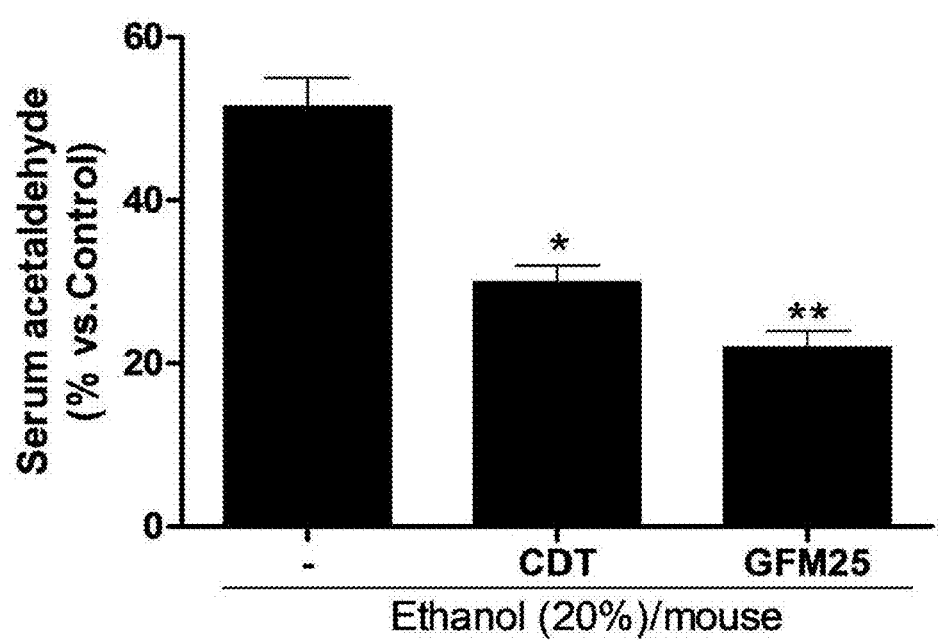
FIG. 18 is a graph showing serum ethanol level of BALB/c mice (administered with 20% ethanol only (−), or with 20% of ethanol and a commercially available hangover reliever (+CDT) or the ginsenoside-free extract of steam-driedKorean ginseng berry according to the present disclosure (+GFM)).

Serum samples of the mice treated with ethanol only, ethanol and CDT or GFM, respectively in Experimental example 4-1 were prepared by collecting blood samples via retro-orbital sinus puncture and transferred to serum separator tubes (Microtainer® Tubes; Becton Dickinson, Franklin Lakes, N.J., USA). Serum was obtained by centrifugation (30 min at 4° C.) at 1200×g, and acetaldehyde and ethanol were determined using either enzymatic or GC analysis. The enzymatic analysis was conducted with ALDH according to the method of Lundquist (Lundquist F. et al., *Biochem. J.*, 68:172-177, 1958; Lundquist F. et al., In: Bergmeier H U (ed) Methods of enzymatic analysis. 2$^{nd}$ ed. Weinheim/New York and London, 230-257, 1974). This enzymatic test for alcohol utilizes the coenzyme NAD and ADH. The amount of NADH formed is stoichiometric to the amount of acetaldehyde. NADH was determined by light absorbance at 365 nm. As a result, acutely-administered ethanol was highly detected by GC within 1 h in the EtOH group (12.2%), whereas the positive control (CDT) and GFM significantly reduced the level of ethanol (FIGS. 16 and 17). Surprisingly, the GFM almost clearly removed the blood ethanol to the same level as the normal control. Coincidently, the GFM significantly reduced serum acetaldehyde converted by ADH (FIG. 18).

Thus, it is strongly suggested that the GFM according to an embodiment of the present disclosure is very effective to enhance ethanol metabolism in a subject by removing ethanol and acetaldehyde from blood and effective for alleviating hangover thereby.

Experimental Example 5: Hepatoprotective Effect of the GFM

In order to investigate hepatoprotective activity of GFM, the present inventor identified hepatic markers after orally administrating ethanol to 9 weeks old male BALB/c mice. GFM suspended in saline solution was orally administrated (25 mg/kg) and CTD dried and then resolved in saline solution (50 mg/kg) was used as positive control (50 mg/kg). Before the administration, the experimental animals fasted 4 hours, and after the administration additional 1 hour of fasting was performed. Forty five minute after the administration, 300 μl of 20% ethanol was administrated orally. Observing mice treated with 20% ethanol only, the mice showed elevated respiration rate, reduced locomotive activity and stagger but showed normal activity as time passed. Eight hours after ethanol treatment blood was collected and serum was isolated by centrifugation at 3,000 rpm at 30 min and then serum levels of GOT and GPT which are main hepatic markers were analyzed by Laboratory Animal Research Center in Chungbuk National University. In addition, in order to investigate whether the animal had side effects according to the administration of drugs, body weights, organ masses were calculated.

There was no abnormal symptom after the administration of drugs, and there was no significant difference of feeding amount, locomotive activity and organ masses among experimental groups (Table 3). Determining serum level of GOT and GPT which are induced when a hepatic lesion occurs through hematobiochemical analysis, the markers were significantly elevated in ethanol treatment group whereas the levels of the markers were reduced in CTD and GFM treatment groups similar as control group (Table 4). This result suggests that GFM is effective for the recovery of liver injured by alcohol. Especially, GOT which is a marker for alcoholic liver disease was reduced in the GFM treatment group under the level of control group, which means that the GFM facilitated ethanol metabolism by inhibiting liver injure effectively.

TABLE 3

Comparison of body weights and organ masses among experimental groups

|  | Ctrl | Ethanol | CTD (50 mg/kg) | GFM (25 mg/kg) |
| --- | --- | --- | --- | --- |
| Body weight (g) | 20.80 ± 0.14 | 21.00 ± 0.57 | 22.20 ± 0.78 | 21.45 ± 0.99 |
| Liver mass (g) | 1.28 ± 0.01 | 1.31 ± 0.11 | 1.44 ± 0.02 | 1.24 ± 0.05 |
| Spleen mass (g) | 0.09 ± 0.01 | 0.09 ± 0.01 | 0.11 ± 0.00 | 0.07 ± 0.01 |

TABLE 4

Hematobiochemical analysis

|  | GOT (IU/L) | GPT (IU/L) |
| --- | --- | --- |
| Ctrl | 71.82 ± 4.84 | 29.61 ± 1.99 |
| 20% Ethanol | 259.00 ± 17.44 | 150.50 ± 10.13 |
| CTD (50 mg/kg) | 78.12 ± 5.26 | 43.05 ± 2.90 |
| GFM (25 mg/kg) | 61.01 ± 4.11 | 38.01 ± 2.56 |

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. A method for alleviating hangover symptoms in a subject in need thereof, the method comprises administering an effective amount of ginsenoside-free ethyl acetate fraction of steam-dried *Panax ginseng* berry extract to the subject.

2. The method according to claim 1, wherein the *Panax ginseng* berry is an immature berry.

3. The method according to claim 2, wherein the *Panax ginseng* berry is harvested from 4 to 6 year-old *Panax ginseng*.

4. The method according to claim 1, wherein the ginsenoside-free extract of steam-dried *Panax ginseng* berry is administered orally or parenterally.

5. The method according to claim 1, wherein the ginsenoside-free ethyl acetate fraction of *Panax ginseng* berry extract is prepared by the following method:

steaming *Panax ginseng* berry;
drying the steamed *Panax ginseng* berry to prepare steam-dried *Panax ginseng* berry;
grinding the steam-dried *Panax ginseng* berry to create a powder;
preparing steam-dried *Panax ginseng* berry extract by extracting the powder with C1 to C4 alcohol or a mixture of water and C1 to C4 alcohol;
fractionating the steam-dried *Panax ginseng* berry extract into an ethyl acetate layer and a water layer by adding ethyl acetate and water to the steam-dried *Panax ginseng* berry extract; and
separating and drying the ethyl acetate layer.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: hADH1B F

<400> SEQUENCE: 1
gtggatgaga atgcagtggc                                                 20

<210> SEQ ID NO 2
<211> LENGTH: 20
```

```
<212> TYPE: DNA
<213> ORGANISM: Artificial Sequence
<220> FEATURE:
<223> OTHER INFORMATION: hADH1B R

<400> SEQUENCE: 2
cattcagtgg cacccaactc                                              20

<210> SEQ ID NO 3
<211> LENGTH: 20
<212> TYPE: DNA
<213> ORGANISM: Artificial Sequence
<220> FEATURE:
<223> OTHER INFORMATION: hALDH1A1 F

<400> SEQUENCE: 3
ggagccaaaa gggtcatcat                                              20

<210> SEQ ID NO 4
<211> LENGTH: 20
<212> TYPE: DNA
<213> ORGANISM: Artificial Sequence
<220> FEATURE:
<223> OTHER INFORMATION: hALDH1A1 R

<400> SEQUENCE: 4
gtgatggcat ggactgtggt                                              20

<210> SEQ ID NO 5
<211> LENGTH: 20
<212> TYPE: DNA
<213> ORGANISM: Artificial Sequence
<220> FEATURE:
<223> OTHER INFORMATION: hCatalase F

<400> SEQUENCE: 5
cagctgacac agttcgggac                                              20

<210> SEQ ID NO 6
<211> LENGTH: 20
<212> TYPE: DNA
<213> ORGANISM: Artificial Sequence
<220> FEATURE:
<223> OTHER INFORMATION: hCatalase R

<400> SEQUENCE: 6
gatgtccatc tggaatcccc                                              20

<210> SEQ ID NO 7
<211> LENGTH: 20
<212> TYPE: DNA
<213> ORGANISM: Artificial Sequence
<220> FEATURE:
<223> OTHER INFORMATION: hCYP2E1 F

<400> SEQUENCE: 7
catgaagcaa cccgagacac                                              20

<210> SEQ ID NO 8
<211> LENGTH: 19
<212> TYPE: DNA
<213> ORGANISM: Artificial Sequence
<220> FEATURE:
<223> OTHER INFORMATION: hCYP2E1 R

<400> SEQUENCE: 8
```
ctgcaaaatg gcacacaac                                              19

<210> SEQ ID NO 9
<211> LENGTH: 20
<212> TYPE: DNA
<213> ORGANISM: Artificial Sequence
<220> FEATURE:
<223> OTHER INFORMATION: hGAPDH F

<400> SEQUENCE: 9
ggagccaaaa gggtcatcat                                             20

<210> SEQ ID NO 10
<211> LENGTH: 20
<212> TYPE: DNA
<213> ORGANISM: Artificial Sequence
<220> FEATURE:
<223> OTHER INFORMATION: hGAPDH R

<400> SEQUENCE: 10
gtgatggcat ggactgtggt                                             20

<210> SEQ ID NO 11
<211> LENGTH: 20
<212> TYPE: DNA
<213> ORGANISM: Artificial Sequence
<220> FEATURE:
<223> OTHER INFORMATION: mADH1B F

<400> SEQUENCE: 11
atttcatggg cgtcagttca                                             20

<210> SEQ ID NO 12
<211> LENGTH: 20
<212> TYPE: DNA
<213> ORGANISM: Artificial Sequence
<220> FEATURE:
<223> OTHER INFORMATION: mADH1B R

<400> SEQUENCE: 12
aagacctaca caccccaggc                                             20

<210> SEQ ID NO 13
<211> LENGTH: 20
<212> TYPE: DNA
<213> ORGANISM: Artificial Sequence
<220> FEATURE:
<223> OTHER INFORMATION: mALDH1A1 F

<400> SEQUENCE: 13
gtggacaaag tggcgttcac                                             20

<210> SEQ ID NO 14
<211> LENGTH: 20
<212> TYPE: DNA
<213> ORGANISM: Artificial Sequence
<220> FEATURE:
<223> OTHER INFORMATION: mALDH1A1 R

<400> SEQUENCE: 14
actggccctg gttgaagaac                                             20

<210> SEQ ID NO 15
<211> LENGTH: 20
<212> TYPE: DNA
<213> ORGANISM: Artificial Sequence
<220> FEATURE:
<223> OTHER INFORMATION: mCatalase F

<400> SEQUENCE: 15
cagcgaccag atgaagcagt                                               20

<210> SEQ ID NO 16
<211> LENGTH: 20
<212> TYPE: DNA
<213> ORGANISM: Artificial Sequence
<220> FEATURE:
<223> OTHER INFORMATION: mCatalase R

<400> SEQUENCE: 16
caggaatccg ctctctgtca                                               20

<210> SEQ ID NO 17
<211> LENGTH: 20
<212> TYPE: DNA
<213> ORGANISM: Artificial Sequence
<220> FEATURE:
<223> OTHER INFORMATION: mCYP2E1 F

<400> SEQUENCE: 17
ctgcatggct acaaggctgt                                               20

<210> SEQ ID NO 18
<211> LENGTH: 20
<212> TYPE: DNA
<213> ORGANISM: Artificial Sequence
<220> FEATURE:
<223> OTHER INFORMATION: mCYP2E1 R

<400> SEQUENCE: 18
acttagggaa aacctccgca                                               20

<210> SEQ ID NO 19
<211> LENGTH: 20
<212> TYPE: DNA
<213> ORGANISM: Artificial Sequence
<220> FEATURE:
<223> OTHER INFORMATION: mGAPDH F

<400> SEQUENCE: 19
tacagcttca ccaccacagc                                               20

<210> SEQ ID NO 20
<211> LENGTH: 20
<212> TYPE: DNA
<213> ORGANISM: Artificial Sequence
<220> FEATURE:
<223> OTHER INFORMATION: mGAPDH R

<400> SEQUENCE: 20
aaggaaggct ggaaaagagc                                               20